United States Patent [19]

Suh et al.

[11] 4,256,761

[45] Mar. 17, 1981

[54] ANTIHYPERTENSIVE AMIDES

[75] Inventors: John T. Suh, Greenwich, Conn.; Jerry W. Skiles, Tuckahoe, N.Y.; Bruce E. Williams, Yorktown Heights, N.Y.; Alfred Schwab, Williston Park, N.Y.

[73] Assignee: USV Pharmaceutical Corporation, Tuckahoe, N.Y.

[21] Appl. No.: 57,175

[22] Filed: Jul. 13, 1979

[51] Int. Cl.³ .................. A61K 31/36; A61K 31/265; C07C 149/43; C07C 149/40
[52] U.S. Cl. ................................ 424/282; 260/455 R; 260/455 B; 260/340.5 R; 424/301; 424/319; 424/311; 560/16; 560/17; 560/9; 560/125; 560/155; 560/153; 562/426; 562/507; 562/556; 564/154
[58] Field of Search ................... 260/340.5 R, 557 R, 260/557 B, 558 S, 561 A, 455 R, 455 B, 609 R; 560/16, 17, 9, 125, 155, 153; 562/507, 556, 426; 424/319, 311, 282, 301

[56] References Cited

U.S. PATENT DOCUMENTS 3,869,492  3/1975  Biel et al. .............................. 424/301

Primary Examiner—Henry R. Jiles
Assistant Examiner—Robert C. Whittenbaugh
Attorney, Agent, or Firm—Leon E. Tenenbaum

[57] ABSTRACT

Compounds of the structure:

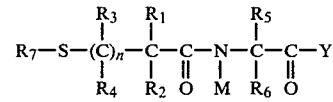

wherein $R_1$, $R_2$, $R_3$, $R_4$, $R_5$, and $R_6$ are hydrogen, alkyl, alkenyl, alkynyl, phenyl-alkyl, or cycloalkyl, n is an integer from 0 to 4 inclusive, M is alkenyl, alkynyl, cycloalkyl, cycloalkyl-alkyl, polycycloalkyl, polycyclo-alkyl-alkyl, aryl, aralkyl, heteroaryl, heteroaryl-alkyl, hetero-cycloalkyl, hetero-cycloalkyl-alkyl, alkoxyalkyl, alkylthioalkyl, alkylamino-alkyl, dialkylamino-alkyl, fused aryl-cycloalkyl, fused aryl-cycloalkyl-alkyl, fused heteroaryl-cycloalkyl, or fused heteroaryl-cycloalkyl-alkyl, Y is hydroxy, alkoxy, amino, or substituted amino, aminoalkanoyl, aryloxy, aminoalkoxy, or hydroxyalkoxy, and $R_7$ is hydrogen, alkanoyl, carboxylalkanoyl, hydroxyalkanoyl, amino-alkanoyl, cyano, amidino, carbalkoxy, ZS, or

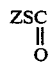

wherein Z is hydrogen, alkyl, hyroxyalkyl, aminoalkyl or the radical

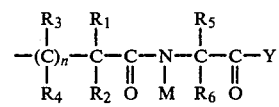

wherein $R_1$, $R_2$, $R_3$, $R_4$, $R_5$, $R_6$, n, M and Y are as described above; and where Y is hydroxy their non-toxic, pharmaceutically acceptable alkali metal, alkaline earth metal, and amine salts.

18 Claims, No Drawings

ANTIHYPERTENSIVE AMIDES

This invention relates to new chemical compounds having valuable pharmaceutical activity. It particularly relates to amides having antihypertensive and angiotensin converting enzyme inhibitory activity and of the structure

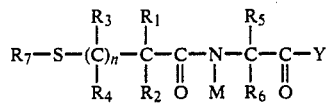

wherein
- $R_1$, $R_2$, $R_3$, $R_4$, $R_5$, and $R_6$ are hydrogen, alkyl, alkenyl, alkynyl, phenyl-alkyl, and cycloalkyl, and may be the same or different,
- n is an integer from 0 to 4 inclusive,
- M is alkenyl, alkynyl, cycloalkyl, cycloalkyl-alkyl, polycycloalkyl, polycycloalkyl-alkyl, aryl, aralkyl, heteroaryl, heteroaryl-alkyl, hetero-cycloalkyl, hetero-cycloalkyl-alkyl, fused aryl-cycloalkyl, fused aryl-cycloalkyl-alkyl, fused heteroaryl-cycloalkyl, fused heteroaryl-cycloalkyl-alkyl, alkoxyalkyl, alkylthioalkyl, alkylamino-alkyl, or dialkylaminoalkyl.
- Y is hydroxy, alkoxy, amino, or substituted amino, aminoalkanoyl, aryloxy, aminoalkoxy, or hydroxyalkoxy, and
- $R_7$ is hydrogen, alkanoyl, carboxyalkanoyl, hydroxyalkanoyl, aminoalkanoyl, cyano, amidino, carbalkoxy, ZS, or

wherein Z is hydrogen, alkyl, hydroxyalkyl, or the radical

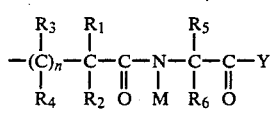

wherein $R_1$, $R_2$, $R_3$, $R_4$, $R_5$, $R_6$, n, M and Y are as described above; and where Y is hydroxy, their non-toxic, pharmaceutically acceptable alkali metal, alkaline earth metal, and amine salts.

The alkyl groups per se and in the alkyl moiety in aralkyl, cycloalkyl-alkyl, polycycloalkyl-alkyl, heteroaryl-alkyl and the like, and, in alkoxy, alkylthio, alkanoyl, carbalkoxy, and alkylamino, may be straight chained or branched and are preferably lower alkyl groups containing from 1 to 6 carbons. Such groups include methyl, ethyl, propyl, isopropyl, butyl, isobutyl, amyl, iso-amyl, hexyl, and the like.

The alkenyl and alkynyl groups may also be branched or straight-chained and contain from 2 to 6 carbon atoms. Such groups include vinyl, ethynyl, propenyl, allyl, isopropenyl, and the like.

The M cycloalkyl, polycycloalkyl, aryl, heteroaryl, aryalkyl, fused aryl-cycloalkyl, groups and the like contain from 3 to 16 carbon atoms and may carry substituents such as lower alkyl, alkenyl, alkynyl, hydroxy, thio, amino, alkoxy, alkylthio, alkyl-amino, and halo. They include such radicals as cyclopropyl, cyclobutyl, cyclopentyl, cyclohexyl, cycloheptyl, adamantyl, nor- bornyl, phenyl, tolyl, benzyl, phenethyl, dimethoxyphenyl, hydroxybenzyl, indanyl, naphthyl, tetrahydronaphthyl, decahydronaphthyl, pyridyl, quinolyl, pyrrolidyl, pyrrolyl, morpholinyl, furyl, furfuryl, tetrahydrofurfuryl, benzimidazolyl, thienyl, imidazolyl, and the like.

The preferred compounds are those wherein $R_1$, $R_3$, $R_4$, $R_5$ and $R_6$ are hydrogen, $R_2$ is lower alkyl, preferably methyl, $R_7$ is hydrogen or lower alkanoyl, n is 1, and Y is hydroxy.

The compounds of the present invention are prepared by the reaction of an appropriately substituted amino acid ester of the structure

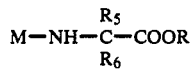

with a carboxylic acid of the structure

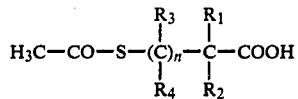

to produce an amide of the structure

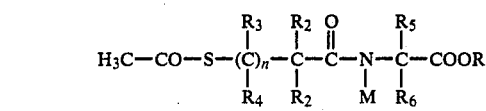

followed by the stepwise hydrolysis of (i) the ester to yield the free carboxylic acid and (ii) the acetyl group to yield the free thiol, providing a compound of the structure

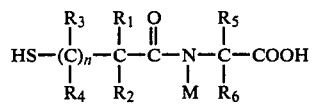

In these formulae, R is lower alkyl, preferably t-butyl and $R_1$, $R_2$, $R_3$, $R_4$, $R_5$, $R_6$, M and n are as defined above.

It is known to those skilled in the art that those amides of the present invention having an asymmetric carbon atom may exist in racemic or optically active levo or dextro forms. All of these forms are contemplated within the scope of this invention.

The invention will be more fully illustrated in the examples which follow. These examples are given by way of illustration and are not be considered as limiting.

EXAMPLE 1 t-Butyl bromoacetate

Bromoacetic acid (484 g, 3.48 mol) was dissolved in methylene chloride (1000 ml) and concentrated sulfuric acid (5 ml) was added as catalyst. The resulting solution was cooled in a dry-ice acetone bath and isobutylene was bubbled through the solution for an hour and a half. The flask was lightly stopped with a gas venting stopper and allowed to stand at room temperature overnight. Aqueous potassium carbonate (10%) was added and the layers were separated. The aqueous layer was discarded and the organic layer was washed once more with aqueous potassium carbonate (10%), once with water, dried over magnesium sulfate, and filtered. Evaporation of the solvent afforded t-butyl bromoacetate as a pale yellow oil (600 g, 88.4%).

EXAMPLE 2

2-Acetylthio-1-methylpropionic acid

Thiolacetic acid (1000 g, 13.2 mol) was placed in a five-liter round bottom flask and cooled in an ice bath. Methacrylic acid (610 g, 7.09 mol) was added with vigorous stirring. Cooling was continued for fifteen minutes and then the reaction mixture was heated to a gentle reflux for one hour. Stirring was continued at room temperature for six days. Excess thiolacetic acid was removed in vacuo and the residue was dissolved in chloroform. The chloroform was washed four times with water and dried over magnesium sulfate. Filtration and evaporation of the solvent yielded a yellowish-orange oil which was vacuum distilled at 110° C. to give the product initially as a yellow oil which slowly crystallized. Addition of ether and filtration of the product afforded a pale yellow solid (890 g, 77.5%), m.p. 35°–37°.

EXAMPLE 3

2-Acetylthio-1-methylpropionyl chloride

2-Acetylthio-1-methylpropionic acid (6.3 g, 0.0389 mol) was dissolved in toluene (50 ml) and five drops of pyridine was added. Thionyl chloride (10 ml.) was added in one portion and the resulting mixture was stirred at room temperature for one and a half hours. The toluene was evaporated on a rotary evaporator and water was added to the residue. The product was extracted three times with chloroform. The combined chloroform extract was washed twice with 5% sodium bicarbonate and twice with water. The chloroform was dried over magnesium sulfate, filtered and evaporated to afford (6.9 g, 98.3%) of the product as a pale yellow oil.

EXAMPLE 4

N-(Cyclopropyl)glycine t-butyl ester

Cyclopropylamine (19.5 g, 0.342 mol) was placed in a pressure bottle and ethanol (100 ml.) was added. The resulting solution was cooled in an ice bath and sodium bicarbonate (8.5 g, 0.101 mol) and t-butyl bromoacetate (15.5 g, 0.0795 mol) was added. The flask was stoppered and the contents of the flask were stirred for 30 minutes with external cooling (ice bath) and then at room temperature overnight. Most of the solvent was removed on a rotary evaporator and water was added to the residue. The product was extracted several times with chloroform. The combined chloroform extract was washed with water, dried over sodium sulfate, filtered and evaporated to yield the product as a pale yellow oil (12.5 g, 92%).

EXAMPLE 5

N-(3-Acetylthio-2-methylpropanoyl)-N-(cyclopropyl)glycine t-butyl ester

To a solution of N-(cyclopropyl)glycine t-butyl ester (12 g, 0.0702 mol) and 3-acetylthio-2-methylpropionic acid (8.1 g, 0.050 mol) in methylene chloride (200 ml) chilled in an ice bath was added dicyclohexylcarbodiimide (14.4 g, 0.070 mol). The resulting mixture was stirred for sixteen hours at room temperature. The dicyclohexylurea was removed by filtration and washed with diethyl ether. Evaporation of the filtrate yielded the crude product as a pale yellow oil which was used without further purification.

EXAMPLE 6

N-(3-Acetylthio-2-methylpropanoyl)-N-(cyclopropyl)glycine

Crude N-(3-acetylthio-2-methylpropanoyl)-N-(cyclopropyl)glycine t-butyl ester (19.5 g, 0.0619 mol) was dissolved in a mixture of anisole (50 ml) and trifluoroacetic acid (250 ml). The resulting red solution was stirred for one and a half hours at room temperature. The solvent was evaporated and the residue was distributed between ethyl acetate and saturated sodium bicarbonate. The aqueous sodium bicarbonate layer was acidified cautiously with concentrated hydrochloric acid to pH 4–5. The precipitated product was extracted into chloroform and washed twice with water. The organic phase was dried over magnesium sulfate, filtered and evaporated to give initially a colorless oil which was crystallized from diethyl ether to afford colorless crystals (9.7 g, 61%), m.p. 86°–88°. The dicyclohexylamine (DCHA) salt was prepared in ether to afford colorless crystals, m.p. 68°–70°.

EXAMPLE 7

N-(3-Mercapto-2-methylpropanoyl)-N-cyclopropylglycine

Anhydrous ammonia was bubbled for fifteen minutes through methanol (350 ml) and the resulting saturated solution was added to N-(3-acetylthio-2-methylpropanoyl)-N-cyclopropylglycine (20 g, 0.0772 mol) and the system was placed under nitrogen. The reaction was stirred at room temperature for an hour and a half. The solvent was removed in vacuo and the residue was applied to a column of AG-50W-X2 (Bio-Rad Laboratories) cation exchange resin and eluted with methanol. The methanol was evaporated and the residue was dissolved in chloroform. The chloroform was washed once with a small amount of water and dried over magnesium sulfate. Filtration and evaporation of the solvent afforded a colorless oil (15 g) which was crystallized from ethyl acetate-n-hexane to afford colorless crystals (14 g, 84%), m.p. 89°–91°. The DCHA salt was prepared in ether, m.p. 123°–125°.

EXAMPLE 8

N-(exo-Norbornyl)glycine t-butyl ester exo-Aminonorbornane (63 g, 0.568 mol) was dissolved in ethanol (350 ml.) and triethylamine (86 g, 0.844 mol) was added. t-Butyl bromoacetate (111 g, 0.568 mol) in ethanol (100 ml) was added dropwise. The resulting mixture was stirred overnight at room temperature. The solvent was evaporated and water was added to the residue. The product was extracted several times into chloroform. The combined chloroform extracts were washed twice with water, dried over magnesium sulfate, filtered and evaporated to afford a yellow oil (90.6 g). On TLC (n-hex/EtoAC/HOAC 30:60:1) this oil indicated a mixture of two products, a non-polar spot ($R_f$=0.538) which is an amine substituted by two molecules of t-butyl bromoacetate, and a polar spot ($R_f$=0.27) which is the desired product. The product was purified by HPLC to give a colorless oil (58 g, 45%).

EXAMPLE 9

N-(3-Acetylthio-2-methylpropanoyl)-N-(exo-norbornyl)glycine t-butyl ester

To a solution of N-(exo-norbornyl) glycine t-butyl ester (40.9 g, 0.162 mol) and 3-acetylthio-2-methylpropionic acid (32.4 g, 0.20 mol) in a mixture of ether-chloroform (1:1, 400 ml) chilled in an ice bath was added portionwise dicyclohexylcarbodiimide (43.5 g, 0.21 mol). After all the diimide was added stirring was continued at room temperature for four hours. Precipitated dicyclohexylurea was filtered and washed with anhydrous ether and the filtrate was concentrated on a rotary evaporator to give a yellow oil. Ether was added to the oil and the resulting mixture was allowed to stand undisturbed to precipitate more dicyclohexylurea. Dicyclohexylurea was filtered and the filtrate evaporated to give the crude product as a colorless oil which was used without further purification.

EXAMPLE 10

N-(3-Acetylthio-2-methylpropanoyl)-N-(exo-norbornyl)glycine

Crude N-(3-acetylthio-2-methylpropanoyl)-N-(exo-norbornyl)glycine tert-butyl ester (70 g, 0.190 mol) was dissolved in a mixture of anisole (100 ml) and trifluoroacetic acid (200 ml). The resulting solution was stirred at room temperature for two hours. The solvent was evaporated in vacuo and the residue was distributed between ethyl acetate and saturated aqueous sodium bicarbonate. The aqueous bicarbonate was washed twice with ethyl acetate and then acidified cautiously with concentrated hydrochloric acid to pH 4–5. The product was extracted several times into chloroform and the chloroform was washed twice with water. The organic phase was dried over magnesium sulfate, filtered and evaporated to give the crude product as an orange oil which was further purified by HPLC, eluting with ethyl acetate/n-hexane/acetic acid (40:60:1), to yield the pure compound as a colorless oil. The DCHA salt was prepared in ether-hexane, m.p. 125°–126°. The product was analyzed as the free acid.

EXAMPLE 11

N-(3-Mercapto-2-methylpropanoyl)-N-(exo-norbornyl)glycine

Anhydrous ammonia was bubbled for fifteen minutes through methanol (300 ml) and the resulting saturated solution was added to N-(3-acetylthio-2-methylpropanoyl)-N-(exo-norbornyl)glycine (24.2 g, 0.0773 mol) and the system was placed under nitrogen. The reaction was stirred at room temperature for one hour. The solvent was removed in vacuo and the residue was applied to a column of AG-50W-X2 (Bio-Rad Laboratories) cation exchange resin and eluted with methanol. Methanol was evaporated and the residue was dissolved in chloroform. The chloroform was washed once with water and dried over magnesium sulfate. Filtration and evaporation of the chloroform afforded an orange oil (18.2 g) which was purified by HPLC using the following solvent system: n-hexane—ethyl acetate—acetic acid (60:39:1). In this manner the pure compound was obtained as a colorless oil (10.1 g, 48.3%), $R_f$=0.136. The DCHA salt was prepared in ether to afford colorless crystals, m.p. 120°–122°. The product was characterized as its DCHA salt.

EXAMPLE 12

1,1'-Dithiobis-(2-methyl-3-propanoyl)-bis-(N-cyclopropyl) glycine

N-(3-Mercapto-2-methylpropanoyl)-N-cyclopropyl glycine (1.8 g, 8.29 mol) was dissolved in chloroform (50 ml) and vigorously stirred. Iodine (2 g) and potassium iodide (2 g) were added to water and stirred for ten minutes after which undissolved inorganic material was filtered and the filtrate added dropwise to the solution of the above mercapto compound until a color remained in the chloroform layer. The resulting mixture was stirred at room temperature for one hour. The layers were separated and the aqueous layer was extracted once with chloroform. The combined chloroform extracts were washed once with aqueous 10% sodium hydrosulfite, twice with water, dried over magnesium sulfate, filtered and evaporated to give the crude product as a colorless oil. The crude product was purified by HPLC using the solvent system of chloroform-acetic acid (85:15) to give the pure product as colorless crystals (0.62 g, 35%) after recrystallization from acetone-ether, m.p. 167°–171°.

EXAMPLE 13

N-(Cyclobutyl)glycine t-butyl ester

An ethanolic solution of t-butyl bromoacetate (39 g, 0.2 mol) was added dropwise to a stirred chilled ethanolic solution containing cyclobutyl amine (28.4 g, 0.4 mol) and triethylamine (25.3 g, 0.25 mol). After stirring overnight at room temperature, the reaction mixture was concentrated and the residue redissolved in methylene chloride (300 ml). This solution was washed with water (3×500 ml), dried over MgSO$_4$, filtered, and evaporated to dryness, yielding 24.9 g (67%) of the desired product as a light brown oil.

EXAMPLE 14

N-(3-Acetylthio-2-methylpropanoyl)-N-cyclobutylglycine t-butyl ester

To a chilled (0.5° C.) methylene chloride solution of N-cyclobutyl-glycine t-butyl ester (63.2 g, 0.34 mol) and triethylamine (26 g, 0.4 mol) was added dropwise 3-acetylthio-2-methylpropanoyl chloride (61.4 g, 0.34 mol). After stirring overnight the reaction mixture was filtered and the filtrate was concentrated. The residue was redissolved in ethyl acetate, washed with 5% HCl (3×500 ml), brine (500 ml) and saturated aqueous sodium bicarbonate (6×600 ml), dried over MgSO$_4$, filtered, and concentrated yielding 80.6 g (72%) of the product as a brown oil.

EXAMPLE 15

N-(3-Acetylthio-2-methylpropanoyl)-N-cyclobutylglycine

To a stirred, argon flushed solution of N-(3-acetylthio-2-methyl-propanoyl)-N-cyclobutylglycine t-butyl ester (28.4 g, 0.086 mol) in methylene chloride was added trimethylsilyl iodide (18.0 g, 0.09 mol). After stirring at room temperature for 40 minutes the reaction was quenched by the addition of 50 ml of water. To this mixture, after stirring for 1 hour, was added 150 ml of 4% aqueous HCl, and the mixture was extracted with methylene chloride. The organic extracts were combined, dried over MgSO$_4$, and evaporated to yield 21.9 g (90%) of the desired product as a light brown oil. This compound was characterized as its DCHA salt, prepared by adding DCHA to an ethereal solution of the compound until bringing the solution to pH 9. The salt was collected and recrystallized in acetonitrile to yield a white crystalline solid, m.p. 162.5°–164.5° C.

EXAMPLE 16

N-(3-Mercapto-2-methylpropanoyl)-N-cyclobutylglycine

Ammonia gas was bubbled through a stirred methanolic solution of N-(3-acetylthio-2-methylpropanoyl)-N-cyclobutylglycine (14.1 g, 0.052 mol) for 1 hour. This reaction mixture was left stirring 1 more hour at room temperature. Concentration on a rotary evaporator removed the remaining ammonia and most of the solvent. The residue was rediluted with methanol (500 ml) and the resultant solution was stirred with Bio-Rad AG-50W-X2 cation exchange resin (200 ml) for 1 hour. Filtration followed by concentration of the filtrate yielded 11 g (91%) of a thick yellow oil. This material was purified by HPLC with ethyl acetate, toluene, hexane, acetic acid (25:15:25:1) as the eluent to afford 8.8 g of the compound as a very viscous colorless oil.

EXAMPLE 17

N-(3-Methylthiopropyl)glycine t-butyl ester

To a mixture of 3-methylthiopropylamine (30.0 g, 0.285 mol) and sodium bicarbonate (12.0 g, 0.142 mol) in 250 ml of ethanol was added dropwise bromo-t-butyl acetate (27.8 g, 0.142 mol). After 5 hours the ethanol was removed on a rotary evaporator and the residue partitioned between water and chloroform. The chloroform layer was dried, filtered and concentrated to give 36.4 g of crude N-(3-methylthiopropyl)glycine t-butyl ester as an oil.

EXAMPLE 18

N-(3-Acetylthio-2-methylpropanoyl)-N-(3-methylthiopropyl)glycine t-butyl ester

To a solution of N-(3-methylthiopropyl)glycine t-butyl ester (36.4 g, 0.166 mol) and triethylamine (20.2 g, 0.199 mol) in 300 ml of dioxane was added dropwise 3-acetylthio-2-methylpropanoyl chloride (30.0 g, 0.166 mol). After stirring at room temperature for 16 hours the mixture was filtered and concentrated to yield 52.9 g. Purification by medium pressure liquid chromatography eluting with 20% ethyl acetate in hexane gave 18.0 g (30%) of N-(3-acetylthio-2-methylpropanoyl)-N-(3-methylthiopropyl)glycine t-butyl ester as a colorless oil. $R_f$=0.19 (20% ethyl acetate in hexane).

EXAMPLE 19

N-(3-Acetylthio-2-methylpropanoyl)-N-(3-methylthiopropyl)glycine

To a solution of N-(3-acetylthio-2-methylpropanoyl)-N-(3-methylthiopropyl)glycine t-butyl ester (18.1 g, 0.05 mol) in 180 ml of methylene chloride was added trimethylsilyl iodide (9.97 g, 0.05 mol). After stirring at room temperature for 1 hour, water and then saturated sodium bicarbonate were added. The layers were separated and the organic phase washed again with saturated sodium bicarbonate solution. The combined aqueous solutions were acidified to pH 2 with concentrated hydrochloric acid and the solution extracted twice with ethyl acetate. The ethyl acetate solution was dried, filtered, and concentrated to give 12.6 g (82%) of N-(3-acethylthio-2-methylpropanoyl)-N-(3-methylthiopropyl)glycine as an oil. The compound was characterized as its DCHA salt, prepared by dissolving the acid in ether and adding dicyclohexylamine to pH 8–9. The salt was isolated as a white crystalline solid, m.p. 120°–121°.

EXAMPLE 20

N-(3-Mercapto-2-methylpropanoyl)-N-(3-methylthiopropyl)glycine

To N-(3-acetylthio-2-methylpropanoyl)-N-(3-methylthiopropyl)glycine (2.0 g, 6.5 mol) was added 30 ml of ammonia-saturated methanol and the resulting solution stirred for 3 hours at room temperature under nitrogen. The solution was then concentrated and partitioned between five percent aqueous sodium bisulfate solution and ethyl acetate. The ethyl acetate solution was washed with brine, dried, filtered and concentrated to give 2.0 g of material which was purified by medium pressure liquid chromatography eluting with 2% acetic acid/49% ethyl acetate/49% hexane to yield 0.8 g of N-(3-mercapto-2-methylpropanoyl)-N-(3-methylthiopropyl)glycine as an oil. The compound was characterized as its DCHA salt, prepared by dissolving the acid in ether and adding the amine to pH 9 and then adding hexane. The salt was isolated as a white crystalline solid m.p. 122°–128°.

EXAMPLE 21

N-(−)-3′-Pinanylmethylglycine t-butyl ester (−)-3-Pinane-methylamine (20.6 g, 0.101 mol) was dissolved in a mixture of acetonitrile (200 ml), water (75 ml) and concentrated ammonium hydroxide (75 ml). t-Butyl bromoacetate (19.8 g, 0.102 mol) in acetonitrile (100 ml) was added dropwise. The resulting mixture was stirred overnight at room temperature. Acetonitrile was evaporated in vacuo and water was added to the residue. The product was extracted several times into chloroform. The combined chloroform extract was washed with water, dried over magnesium sulfate, filtered and evaporated to give a yellowish-green oil (25.0 g, 88%) which was used without further purification.

EXAMPLE 22

N-(3-Acetylthio-2-methylpropanoyl)-N-(−)-3′-pinanylmethylglycine t-butyl ester

To a solution of N-(−)-3′-pinanylmethylglycine t-butyl ester (14.8 g, 0.0527 mol) and 3-acetylthio-2-methylpropionic acid (9.72 g, 0.060 mol) in anhydrous ether (250 ml) chilled in an ice bath was added portionwise dicyclohexylcarbodiimide (12.5 g, 0.0607 mol). After all the diimide was added stirring was continued at room temperature for four hours. Precipitated dicyclohexylurea was filtered and washed with anhydrous ether. The filtrate was concentrated to give a pale yellow oil which was used without further purification.

EXAMPLE 23

N-(3-Acetylthio-2-methylpropanoyl)-N-(−)-3′-pinanylmethylglycine

Crude N-(3-acetylthio-2-methylpropanoyl)-N-(−)-3′-pinanylmethylglycine t-butyl ester (1.0 g, 0.023 mol) was dissolved in a mixture of anisole (20 ml) and trifluroacetic acid (75 ml). The resulting solution was stirred at room temperature for one hour. Most of the trifluoroacetic acid was evaporated on a rotary evaporator. The residue was distributed between ethyl acetate and saturated sodium bicarbonate. The aqueous bicarbonate phase was separated and washed twice with ethyl acetate and then acidified cautiously with concentrated hydrochloric acid to pH 4–5. The precipitated product was extracted into chloroform and washed several times with water. The organic extract was dried over magnesium sulfate, filtered and evaporated to give a thick oil (4 g). The product was further purified by HPLC (Waters Associates) and the product was eluted with ethyl acetate/hexane/acetic acid (40:60:1) to give the desired product initially as a colorless oil which on standing changed to colorless crystals which were filtered and washed with ether, m.p. 117°.

EXAMPLE 24

N-(-3-Mercapto-2-methylpropanoyl)-N-(−)-3'-pinanylmethylglycine

N-(3-Acetylthio-2-methylpropanoyl)-N-(−)-3'-pinanylmethylglycine (4.1 g, 0.011 mol) was placed in a round bottom flask (500 ml) to which a nitrogen inlet was attached. Anhydrous ammonia was bubbled through methanol (150 ml) for twenty minutes. The methanolic ammonia was added to the acid and the flask was placed under a gentle stream of nitrogen. The resulting solution was stirred at room temperature for approximately one hour. Most of the methanol was then evaporated and the residue was passed through a cation exchange column (AG-50W-X2, Bio-Rad Laboratories) and the product was eluted with methanol. The methanol was evaporated and chloroform was added to the residue. The chloroform was washed with water and dried over magnesium sulfate. Filtration and evaporation of the solvent afforded a colorless oil which was purified by HPLC, ethyl acetate/n-hexane/acetic acid (30:60:1) to give the product (3.1 g, 84%) as a colorless oil.

EXAMPLE 25

N-(+)-3'-pinanylmethylglycine t-butyl ester (+)-3-Pinanemethylamine (20.4 g, 0.100 mol) was dissolved in a mixture of acetonitrile (200 ml)-water (75 ml) and concentrated ammonium hydroxide (75 ml). t-Butyl bromoacetate (19.5 g, 0.100 mol) in acetonitrile (100 ml) was added dropwise. The resulting mixture was stirred overnight at room temperature. Acetonitrile was evaporated in vacuo and water was added to the residue. The product was extracted several times with chloroform. The combined chloroform extract was washed with water, dried over magnesium sulfate, filtered and evaporated to give crude pale yellow oil (27.1 g, 95%) which was used without further purification.

EXAMPLE 26

N-(3-Acetylthio-2-methylpropanoyl)-N-(+)-3'-pinanylmethylglycine tert-butyl ester To a solution of N-(+)-3'-pinanylmethylglycine tert-butyl ester (10.7 g, 0.0381 mol) and 3-acetylthio-2-methyl propionic acid (6.2 g, 0.0381 mol) in ether (200 ml) chilled in an ice bath was added portionwise dicyclohexylcarbodiimide (8.3 g, 0.0403 mol). After all the diimide was added stirring was continued at room temperature for four hours. Precipitated dicyclohexylurea was filtered and washed with anhydrous ether. The filtrate was concentrated to give crude light colored oil which was used without further purification.

EXAMPLE 27

N-(3-Acetylthio-2-methylpropanoyl)-N-(+)-3'-pinanylmethylglycine

Crude N-(3-acetylthio-2-methylpropanoyl)-N-(+)-3'-pinanylmethylglycine t-butyl ester (5.0 g, 0.0118 mol) was dissolved in mixture of anisole (10 ml) and trifluoroacetic acid (25 ml). The resulting solution was stirred at room temperature for one hour. The trifluoroacetic acid was removed by evaporation on a rotary evaporator. The residue was distributed between ethyl acetate and saturated sodium bicarbonate. The aqueous bicarbonate phase was separated and washed twice with ethyl acetate and then acidified cautiously with concentrated hydrochloric acid to pH 5. The precipitated product was extracted into chloroform and washed twice with water. The organic phase was dried over magnesium sulfate, filtered and evaporated to give an orange oil (2.9 g). This oil was purified by HPLC and the product was eluted with ethyl acetate/n-hexane/acetic acid (40%/58%/2%) to give the product (1.6 g, 37%) initially as a colorless oil which on standing overnight changed to colorless crystals. Ether was added and the crystals were filtered, m.p. 120°.

EXAMPLE 28

N-(3-Mercapto-2-methylpropanoyl)N-(+)-3'-pinanylmethylglycine (2)

N-(2-Acetylthio-2-methylpropanoyl)-N-(+)-3'-pinanylmethylglycine (10.0 g, 0.0279 mol) was placed in a round bottom flask (500 ml) to which a nitrogen inlet was attached. Anhydrous ammonia was bubbled through methanol (400 ml) for ten minutes. The methanolic ammonia was added to the acid in one portion and the flask was placed under a gentle stream of nitrogen. The resulting solution was stirred at room temperature for two hours. Most of the methanol was evaporated and the residue was passed through a cation exchange column (AG-50W-X2, Bio-Rad Laboratories) and the product was eluted with methanol. The methanol was evaporated and chloroform was added to the residue. The chloroform was washed once with water and dried over magnesium sulfate. Filtration and evaporation of the solvent afforded a colorless oil (9.3 g). The oil was purified by HPLC, ethyl acetate/n-hexane/acetic acid (30:60:1), to give the product (5.8 g, 64%) as a colorless oil.

EXAMPLE 29

N-(Nopinyl)glycine t-butyl ester

Nopinylamine (64.2 g, 0.461 mol) was dissolved in a mixture of acetonitrile (250 ml), water (110 ml) and ammonium hydroxide (110 ml). t-Butyl bromoacetate (90.4 g, 0.464 mol) in ethanol (200 ml) was added dropwise. The resulting mixture was stirred at room temperature overnight. The solvent was evaporated and water was added to the residue. The product was extracted several times with chloroform. The combined chloroform extracts were washed twice with water, dried over magnesium sulfate, filtered and evaporated to yield a yellow oil (93.2 g). The product was purified by HPLC (ethyl acetate/n-hexane/acetic acid), (30:60:1) to give a pure colorless oil (72 g, 62%).

EXAMPLE 30

N-(3-Acetylthio-2-methylpropanoyl)-N-nopinylglycine t-butyl ester

To a solution of N-(nopinyl)glycine t-butyl ester (40.9 g, 0.162 mol) and 3-acetylthio-2-methylpropionic acid (32.4 g, 0.20 mol) in a mixture of ether-chloroform (1:1, 400 ml) chilled in an ice bath was added dicyclohexylcarbodiimide (43.3 g, 0.21 mol) portionwise. After all the diimide was added stirring was continued at room temperature for four hours. Precipitated dicyclohexylurea was filtered and washed with anhydrous ether. Evaporation of the filtrate yielded a yellow oil which was used in the next reaction without further purification.

EXAMPLE 31

N-(3-Acetylthio-2-methylpropanoyl)-N-nopinylglycine

Crude N-(3-acetylthio-2-methylpropanoyl)-N-nopinylglycine t-butyl ester (31.5 g) was dissolved in a mixture of anisole (28 ml) and trifluoroacetic acid (71 ml). The resulting solution was stirred at room temperature for five hours. The trifluoroacetic acid was evaporated in vacuo and the residue was distributed between ethyl acetate and saturated aqueous sodium bicarbonate. The aqueous bicarbonate was washed twice with ethyl acetate and then acidified to pH 4–5 with concentrated hydrochloric acid. The product was extracted several times with chloroform and the chloroform was washed twice with water. The organic phase was dried over magnesium sulfate, filtrated and evaporated to give a yellow oil (8.6 g) which was further purified by HPLC eluting with ethyl acetate/n-hexane/acetic acid (40:60:1), to give a colorless oil (6.5 g). The product was purified as its DCHA salt which was prepared in ether-hexane to yield colorless crystals, m.p. 134°–138°.

EXAMPLE 32

N-Cycoheptylglycine t-butyl ester

To a chilled (0°–5° C.) and stirred ethereal solution (500 ml) containing a cycloheptyl amine (25 g, 0.22 mol) and triethylamine (30.3 g, 0.3 mol) was added t-butyl bromoacetate (31.2 g, 0.16 mol) dissolved in ether (100 ml). After six hours, the reaction mixture was diluted with dioxane (300 ml) and concentrated to remove ether. The residue was diluted to 500 ml with dioxane. The mixture was then filtered to remove triethylamine hydrobromide and the filtrate was concentrated to dryness. The residue was dissolved in methylene chloride (400 ml) and washed with saturated aqueous sodium bicarbonate (2×500 ml), brine (500 ml), water (2×500 ml), and brine (500 ml). The organic layer was separated, dried over $Na_2SO_4$ and $MgSO_4$, filtered and concentrated to yield 32.9 g (90%) of the desired compound as a brownish oil.

EXAMPLE 33

N-(3-Acetylthio-2-methylpropanoyl)-N-cycloheptylglycine t-butyl ester

To a stirred and chilled (0°–5° C.) solution of N-cycloheptylglycine t-butyl ester (32.9 g, 0.12 mol) and triethyl amine (13.2 g, 0.13 mol) in methylene chloride (150 ml) was added dropwise 3-acetylthio-2-methylpropanoyl chloride (21.6 g, 0.12 mol) dissolved in 50 ml methylene chloride. The reaction mixture was stirred overnight. Filtration of the reaction mixture followed by washing the filtrate with saturated sodium bicarbonate (500 ml), brine (500 ml), 5% HCL (4×500 ml), brine (500 ml), saturated aqueous sodium bicarbonate (3×500 ml), brine (500 ml); drying the organic layer over $Na_2SO_4$ and $MgSO_4$; filtration; and solvent evaporation afforded a nearly quantitative yield of the desired compound (44 g, crude).

EXAMPLE 34

N-(3-Acetylthio-2-methyl propanoyl)-N-cycloheptylglycine

N-(3-Acetylthio-2-methylpropanoyl)-N-cycloheptylglycine t-butyl ester (33.4 g, 0.09 mol), trimethylsilyl chloride (14.7 g, 0.135 mol), and sodium iodide (20.25 g, 0.135 mol) were added to 50 ml of acetonitrile, and the mixture was stirred for 30 minutes at 50° C. The reaction was then quenched by the addition of 50 ml water, and the mixture was concentrated. The residue was dissolved in saturated aqueous sodium bicarbonate, and was washed several times with ether. The aqueous portion was then separated, acidified (HCl), and extracted several times with methylene chloride. The organic extracts were combined, dried over $MgSO_4$, filtered and concentrated to yield 24 g (86%) of the desired acid. This compound was characterized as its DCHA salt which was prepared by adjusting to pH 9 an ethereal solution of the compound with DCHA. The crude salt was obtained as an off-white crystalline solid. Recrystallization from acetonitrile afforded the salt as a white crystalline solid, m.p. 116°–117° C.

EXAMPLE 35

N-(3-Mercapto-2-methylpropanoyl)-N-cycloheptylglycine

Ammonia gas was bubbled slowly through a stirred methanolic solution of N-(3-acetylthio-2-methylpropanoyl)-N-cycloheptyl glycine (7.2 g, 0.023 mol) for two hours. The reaction mixture was then concentrated and the residue redissolved in methylene chloride (300 ml). This solution was washed with 5% aqueous sodium bisulfate (5×200 ml), dried over $MgSO_4$, filtered and concentrated to yield 5.5 g (88%) crude product. This material was purified further by HPLC, with ethyl acetate/toluene/hexane/acetic acid (50:25:50:2) as the eluent. $R_f$ 0.5 (Toluene/Acetic Acid, 7:3), $R_f$ 0.3 (Ethyl acetate/hexane, acetic acid 50;50;2).

EXAMPLE 36

N-Cylohexylglycine t-butyl ester

To a mixture of cyclohexylamine (61.0 g, 0.615 mol) and sodium bicarbonate (12.9 g, 0.154 mol) in 200 ml of ethanol was added dropwise t-butyl bromoacetate (30.0 g, 0.154 mol). After 72 hours the ethanol was evaporated and the residue partitioned between water and chloroform. The chloroform layer was washed with water, dried, filtered and concentrated under vacuum to give 31.9 g (97%) of N-cyclohexylglycine t-butyl ester as an oil, $R_f$=0.59 (25% acetone/25% ethyl acetate/50% hexane).

EXAMPLE 37

N-(3-Acetylthio-2-methylpropanoyl)-N-cyclohexylglycin t-butyl ester

To a solution of N-cyclohexylglycine t-butyl ester (32.0 g, 0.15 mol) and triethylamine (18.2 g, 0.18 mol) in 500 ml of dioxane was added dropwise 3-acetylthio-2- methylpropanoyl chloride (27.1 g, 0.15 mol). After stirring at room temperature for 16 hours, the mixture was filtered and concentrated to yield 47.6 g (88%). This material was purified by medium pressure liquid chromatography, eluting with 14% ethyl acetate/cyclohexane, to yield 36.4 g (67.9%) of N-(3-acetylthio-2-methyl)-N-cyclohexylglycine t-butyl ester as an oil, $R_f=0.21$ (14% ethyl acetate/hexane).

EXAMPLE 38

N-(3-Acetylthio-2-methylpropanoyl)-N-cyclohexylglycine

To a solution of N-(3-acetylthio-2-methylpropanoyl)-N-cyclohexylglycine t-butyl ester (36.4 g, 0.101 mol) in 300 ml of methylene chloride was added trimethylsilyl iodide (20.4 g, 0.102 mol). After stirring at room temperature for 1.75 hours 50 ml of water was added, followed in 10 min. by 500 ml of saturated sodium bicarbonate solution. An emulsion formed which was separated by centrifuging. The aqueous solution was separated, acidified with concentrated hydrochloric acid, and extracted with ethyl acetate. The extracts were dried, filtered, and concentrated to yield 25.6 g (83.4%) of N-(3-acetylthio-2-methylpropanoyl)-N-cyclohexylglycine as a pale yellow oil. The compound was characterized as its DCHA salt, prepared by dissolving the acid in ether and adding DCHA to pH 8–9. The salt was isolated as a white crystalline solid, m.p. 142°–144°.

EXAMPLE 39

N-(3-Mercapto-2-methylpropanoyl)-N-cyclohexylglycine

To N-(3-Acetylthio-2-methylpropanoyl)-N-cyclohexylglycine (5.1 g, 16.9 mol) was added 100 ml of ammonia-saturated methanol, and the resulting solution stirred for 2.5 hours at room temperature under nitrogen. The solution was concentrated and the residue dissolved in methanol and passed through a column of AG-50W-X2 cation exchange resin. Those fractions showing a positive nitroprusside test were combined and concentrated. This material was then purified by medium pressure liquid chromatography eluting with ethyl acetate/hexane/acetic acid, 48:48:2 to give 0.7 g of N-(3-mercapto-2-methylpropanoyl)-N-cyclohexylglycine as an oil. The compound was characterized as its DCHA salt, prepared by dissolving the acid in ether and adding DCHA to pH 9. The salt was isolated as a white crystalline solid, m.p. 158°–160°.

EXAMPLE 40

N-Cyclopentylglycine t-butyl ester

To a chilled (0°–5° C.) and stirred ethereal solution (500 ml) containing cyclopentyl amine (75 g, 0.88 mol) and triethyl amine (101 g, 1.0 mol) was added t-butyl bromoacetate (136.5 g, 0.7 mol) in ether (300 ml). The reaction mixture was stirred overnight. The ethereal mixture was then concentrated and the residue redissolved in methylene chloride (750 ml). This solution was washed with saturated aqueous sodium bicarbonate (1000 ml), water (2×3000 ml), and brine (2000 ml). The organic portion was separated, dried over MgSO4, filtered and evaporated yielding N-cyclopentylglycine t-butyl ester (92 g, 66%) as a brown oil which slowly crystallized on standing.

EXAMPLE 41

N-(3-Acetylthio-2-methylpropanoyl)-N-cyclopentylglycine t-butyl ester

To a stirred and chilled (0°–5° C.) solution of N-cyclopentylglycine t-butyl ester (60 g, 0.3 mol) and triethylamine (75 ml, 0.5 mol) in methylene chloride (200 ml) was added dropwise 3-acetylthio-2-methylpropanoyl chloride (54 g, 0.3 mol) dissolved in methylene chloride (250 ml). The reaction mixture was stirred overnight. It was filtered free of solid material which was then washed with fresh methylene chloride. Washings and filtrate were combined and concentrated. The residue was dissolved in ethyl acetate and washed with saturated aqueous sodium bicarbonate (1000 ml), brine (600 ml), 5% HCl (3×500 ml), brine (500 ml), saturated sodium bicarbonate (5×500 ml). The organic layer was now separated, dried (Na2SO4 and MgSO4), filtered and concentrated to yield the desired product (80.1 g, 78%) as a brown oil.

EXAMPLE 42

N-(3-Acetylthio-2-methylpropanoyl)-N-cyclopentylglycine

N-(3-Acetylthio-2-methylpropanoyl)-N-cyclopentylglycine t-butyl ester (80.1 g, 0.23 mol), trimethylsilyl chloride (37.9 g, 0.35 mol), and sodium iodide (52.5 g, 0.35 mol) were added to acetonitrile (300 ml), and the reaction mixture was stirred at 45° C.–50° C. for 30 minutes. Water (50 ml) was then added and the mixture was concentrated. The residue was dissolved in saturated aqueous sodium bicarbonate (400 ml) and was washed with ethyl acetate (3×400 ml). The aqueous portion was separated, acidified (conc. hydrochloric acid), and extracted with ethyl acetate. The organic extracts were combined, dried over Na2SO4 and MgSO4, filtered and concentrated yielding the crude desired product as a brown oil (60 g, 90%). When this material was eluted through a high pressure liquid chromatography column with ethyl acetate/hexane/acetic acid (60:40:2) a slightly yellow oil was obtained. This compound was characterized as its DCHA salt which was prepared by adjusting to pH 9 an acetonitrile solution of the compound with DCHA. The salt was obtained as a white crystalline solid, m.p, 172°–174° C.

EXAMPLE 43

N-(3-Mercapto-2-methyl propanoyl)-N-cyclopentylglycine

Ammonia gas was bubbled through a methanolic solution of N-(3-acetylthio-2-methylpropanoyl)-N-cyclopentylglycine (10.4 g, 0.036 mol) for one hour. The reaction mixture was then stoppered and stirred for 30 more minutes and then concentrated. The residue was redissolved in ethyl acetate (400 ml) and was washed with 5% aqueous sodium bisulfate (3×150 ml). The organic portion was then removed, dried (MgSO4), filtered and concentrated. The crude material was further purified by HPLC with ethyl acetate, toluene, hexane, acetic acid (50:25:50:2) as the eluent. The desired product was isolated as a nearly colorelss oil (pale yellowish tinge). 7.9 g (90%) was so obtained.

EXAMPLE 44

N-(2-Benzoylthiopropanoyl)-N-cyclopropylglycine tert-butyl ester

To a solution of N-(cyclopropyl)glycine tert-butyl ester (14.0 g, 0.0824 mol) and (2-benzoylthio) propionic acid (17.3 g, 0.0824 mol) in dry methylene chloride (150 ml) chilled in an ice bath was added portionwise dicyclohexylcarbodiimide (17.0 g, 0.0825 mol). After all the diimide was added, stirring was continued with external cooling for 30 minutes and then at room temperature for two days. Precipatated dicyclohexylurea was filtered and washed with anhydrous ether. The filtrate was concentrated in vacuo to give the crude condensed ester as a pale yellow oil (17.1 g) which was used without further purification.

EXAMPLE 45

N-(2-Benzoylthiopropanoyl)-N-cyclopropylglycine

Crude N-(2-benzoylthiopropanoyl)-N-cyclopropylglycine tert-butyl ester (17.1 g) was dissolved in a mixture of anisole (25 ml) and trifluoroacetic acid (100 ml). The resulting solution was stirred at room temperature for two hours. Trifluoroacetic acid was removed in vacuo and the residue was distributed between ethyl acetate and saturated sodium bicarbonate. The aqueous bicarbonate phase was separated and washed twice with ethyl acetate and then acidified cautiously to pH 4–6 with concentrated hydrochloric acid. The precipitated product was extracted into chloroform and washed twice with water. The organic phase was dried over magnesium sulfate, filtered and evaporated to give crude product as a pale yellow oil. The product was characterized as its DCHA salt which was prepared in ether to give colorless crystals, m.p. 140°–143° C.

EXAMPLE 46

N-(3-Acethylthio-2-methylpropanoyl)-N-cyclopropyl-(dl)-alanine tert-butyl ester

To a solution of N-(cyclopropyl)-(dl)-alanine tert-butyl ester (23.6 g, 0.128 mol) and 3-acetylthio-2-methylpropronic acid (20.7 g, 0.128 mol) in dry methylene chloride (150 ml) chilled in an ice bath was added portionwise dicyclohexylcarbodiimide (31.1 g, 0.151 mol). After all the diimide was added stirring was continued at room temperature overnight. Precipitated dicyclohexylurea was filtered and washed with anhydrous ether. The filtrate was concentrated to give the crude product as an auburn oil which was used without further purification.

EXAMPLE 47

N-(3-Acetylthio-2-methylpropanoyl)-N-cyclopropyl-(dl)-alanine

Crude N-(3-acetylthio-2-methylpropanoyl)-N-cyclopropyl-(dl)-alanine tert-butyl ester (60.2 g) was dissolved in a mixture of anisole (54 ml) and trifluoroacetic acid (96 ml). The resulting solution was stirred at room temperature for one hour. Trifluoroacetic acid was removed in vacuo and the residue was distributed between ethyl acetate and saturated sodium bicarbonate. The aqueous bicarbonate phase was separated and washed twice with ethyl acetate and then acidified to pH 4–5 with concentrated hydrocloric acid. The precipitated product was extracted into chloroform and washed twice with water. The organic phase was dried over magnesium sulfate, filtered and evaporated to give the crude acid as a thick yellow oil (22.9 g). The crude product was purified by HPLC, eluting with ethyl acetate/n-hexane/acetic acid (40:60:1), to give pure product as initially a pale yellow oil (9.6 g). The product was crystallized from ether/n-hexane to give colorless crystals, m.p. 83°–85° C.

EXAMPLE 48

N-(3-Mercapto-2-methylpropanoyl)-N-cyclopropyl-(dl)-alanine

Anhydrous ammonia was bubbled through methanol (250 ml) for ten minutes and the resulting saturated solution was added to N-(3-acetylthio-2-methylpropanoyl)-N-cyclopropyl-(dl)-alanine (5.9 g, 0.0216 mol) and the system was placed under nitrogen. The reaction mixture was stirred at room temperature for an hour and a half. The solvent was removed in vacuo and the residue was applied to a column of AG-50W-X2 (Bio-Rad Laboratories) cation exchange resin and eluted with methanol. Methanol was evaporated and the residue was dissolved in chloroform. The chloroform was washed once with water and dried over magnesium sulfate. Filtration and evaporation of the solvent afforded crude product as a yellow oil (4.8 g) which was prufied by HPLC using the following solvent system: n-hexane/ethyl acetate/acetic acid (60:35:1). In this manner pure product was obtained as a colorless oil (3.5 g, 72%). The product was characterized as its dicyclohexylamine salt which was prepared in ether to give colorless crystals, m.p. 129°–130.5° C.

EXAMPLE 49

N-(3-Acetylthio-2-methylpropanoyl)-N-furfurylglycine

Crude N-(3-acetylthio-2-methylpropanoyl)-N-furfurylglycine tert-butyl ester (14.6 g, 0.0407 mol) was dissolved in a mixture of anisole (20 ml) and trifluoroacetic acid (65 ml). The resulting solution was stirred at room temperature for two hours. The solvent was evaporated in vacuo and the residue was distributed between ethyl acetate and saturated aqueous sodium bicarbonate. The aqueous bicarbonate extract was washed twice with ethyl acetate and then acidifed cautiously with concentrated hydrochloric acid to pH 4–5. The product was extracted several times into chloroform and the chloroform was washed twice with water. The organic phase was dried over magnesium sulfate, filtered and evaporated to give crude product as a pale yellow oil which was purified by HPLC using the following solvent system: ethyl acetate/n-hexane/acetic acid (40:60:1) to give pure product as a colorless oil (5.5 g, 44.7%). The product was purified by its DCHA salt which was prepared in ether, m.p. 140°–141° C.

EXAMPLE 50

N-(3-Mercapto-2-methylpropanoyl)-N-furfurylglycine

Anhydrous ammonia was bubbled for ten minutes through methanol (200 ml) and the resulting ammonia saturated solution was added in one portion to N-(3-acetylthio-2-methylpropanoyl)-N-furfurylglycine (8 g, 0.0264 mol) and the resulting colorless solution was placed under nitrogen. The resulting solution was stirred at room temperature for one and a half hours. The solvent was removed in vacuo and the residue was applied to a column of AG-50W-X2 (Bio-Rad Laboratories) cation exchange resin and eluted with methanol. Methanol was evaporated and the residue was dissolved in chloroform. The chloroform was washed once with water and dried over magnesium sulfate. Filtration and evaporation of the solvent afforded crude product as an oil which was purified by HPLC using the following solvent system: ethyl acetate/n-hexane/acetic acid (35:60:1), to give pure colorless oil (5.4 g, 80%). The product was characterized as its DCHA salt, m.p. 150°–153° C.

EXAMPLE 51

N-(3-Acetylthio-2-methylpropanoyl)-N-tetrahydrofurfurylglycine tert-butyl ester

To a solution of N-tetrahydrofurfurylglycine tert-butyl ester (6.6 g, 0.0307 mol) and 3-acetylthio-2-methylpropionic acid (5.3 g, 0.0327 mol) in dry methylene chloride (150 ml) chilled in an ice bath was added dicyclohexylcarbodiimide (6.7 g, 0.0325 mol). The resulting mixture was stirred with cooling for 30 minutes and then overnight at room temperature. Precipitated dicyclohexylurea was filtered and washed with a small amount of methylene chloride. Concentration of the filtrate afforded crude product as a thick yellow oil which was used without further purification.

EXAMPLE 52

N-(3-mercapto-2-methylpropanoyl)-N-tetrahydrofurfurylglycine

Anhydrous ammonia was bubbled for fifteen minutes through methanol (150 ml) and the resulting ammonia saturated solution was added in one portion to N-(3-acetylthio-2-methylpropanoyl)-N-tetrahydrofurfurylglycine (7 g, 0.0231 mol) and the system was placed under a slight pressure of nitrogen. The resulting solution was stirred at room temperature for two hours. The solvent was removed in vacuo and the residue was applied to a column of AG-50W-X2 (Bio-Rad Laboratories) cation exchange resin and eluted with methanol. Methanol was evaporated and the residue was dissolved in chloroform. The chloroform was washed once with water and dried over magnesium sulfate. Filtration and evaporation of the solvent afforded a yellowish-orange oil which was purified by HPLC using the following solvent system: ethyl acetate/n-hexane/acetic acid (40:60:1). In this manner pure product was obtained as a colorless oil (3.9 g, 64%). The product was characterized as its DCHA salt, recrystallized from isopropanol, m.p. 128°–130° C.

EXAMPLE 53

N-(3-Acetylthio-2-methylpropanoyl)-N-(3,4-dimethoxy-β-phenethylgylcine tert-butyl ester To a solution of N-(3,4-dimethoxyphenethyl)glycine tert-butyl ester (26.8 g, 0.091 mol) and 3-acetylthio-2-methylpropionic acid (14.7 g, 0.091 mol) in methylene chloride (300 ml) chilled in an ice bath was added portionwise dicyclohexylcarbodiimide (18.7 g, 0.091 mol). After all the diimide was added stirring was continued at room temperature for four hours. Precipitated dicyclohexylurea was filtered and washed with a small amount of methylene chloride. The filtrate was evaporated to afford crude product as a thick orange oil (47.5 g) which was used without further purification.

EXAMPLE 54

N-(3-Acetylthio-2-methylpropanoyl)-N-(3,4-dimethoxy-β-phenethyl)glycine

Crude N-(3-acetylthio-2-methylpropanoyl)-N-(3,4-dimethoxy-β-phenethylglycine tert-butyl ester (45.7 g., 0.104 mol) was dissolved in a mixture of anisole (45 ml) and trifluoroacetic acid (125 ml). The resulting red solution was stirred for 2 hours at room temperature. The solvent was evaporated in vacuo and the residue was distributed between ethyl acetate and saturated aqueous sodium bicarbonate. The aqueous bicarbonate layer was washed twice with ethyl acetate and then acidified to pH 5 by the cautious addition of concentrated hydrochloric acid. The precipitated product was extracted into chloroform. The chloroform was washed twice with water and dried over magnesium sulfate. Filtration and evaporation of the solvent afforded a yellow oil which was purified by column chromatography over silica-gel using toluene-acetic acid (7:3) as eluent to afford pure product as a colorless oil (24.8 g., 62%). The product was charaterized as its DCHA salt which was prepared in ether to afford colorless crystals, m.p. 117°–118° C.

EXAMPLE 55

N-(3-Mercapto-2-methylpropanoyl)-N-(3,4-dimethoxy-β-phenthyl)glycine

N-(Acetylthio-2-methylpropanoyl)-N-(3,4-dimethoxy-β-phenethylglycine (9.6 g., 0.025 mol) was dissolved in methanol (25 ml) and then concentrated ammonium hydroxide (75 ml) was added. The resulting mixture was stirred under nitrogen for one hour at room temperature. Most of the methanol and water was evaporated and the residue was passed through a cation exchange column, AG-50W-X2 (Bio-Rad Laboratories), and the product was eluted with methanol. Methanol was evaporated and the residue was dissolved in chloroform. The chloroform was washed once with a small amount of water and dried over magnesium sulfate. Filtration and evaporation of the solvent afforded the product as a colorless oil (7.3 g, 86%). The product was characterized as its DCHA salt which was prepared in ether to afford colorless crystals m.p. 127°–129° C.

EXAMPLE 56

N-(3-Acetylthio-2-methylpropanoyl)-N-benzylglycine

Crude N-(3-acethylthio-2-methylpropanoyl)-N-benzylglycine tert-butyl ester (17.0 g, 0.052 mol) was dissolved in a mixture of anisole (35 ml) trifluoroacetic acid (80 ml). The resulting red solution was stirred for two hours at room temperature. The solvent was evaporated and the residue was distributed between ethyl acetate and saturated sodium bicarbonate. The aqueous sodium bicarbonate layer was acidified cautiously with concentrated hydrochloric acid to pH 4–5. The product was extracted several times into chloroform, washed with water, and dried over magnesium sulfate. Filtration and evaporation of the extract afforded the crude product as a yellow oil (6 g) which was further purified by HPLC, eluting with ethyl acetate/n-hexane/acetic acid (40:60:1), to afford the pure product (4.3 g) as a yellow oil. The product was characterized as its dicyclohexylamine salt which was prepared in ether, m.p. 168°–170° C.

EXAMPLE 57

N-(3-Mercapto-2-methylpropanoyl)-N-benzylglycine

Anhydrous ammonia was bubbled for ten minutes through methanol (100 ml) and the resulting saturated solution was added to N-(3-acetylthio-2-methylpropanoyl)-N-benzylglycine (3.5 g, 0.0113 mol). The resulting solution was placed under nitrogen and stirred at room temperature for one hour. The solvent was removed in vacuo and the residue was applied to a column of AG-50W-X2 (Bio-Rad Laboratories) cation exchange resin and eluted with methanol. Methanol was evaporated and the residue was dissolved in chloroform. The chloroform was washed once with water and dried over magnesium sulfate. Filtration and evaporation of the solvent afforded the product as a colorless oil. The product was further purified by HPLC using n-hexane/ethyl acetate/acetic acid (40:60:1) as eluant to give the product as a colorless oil (2.5 g, 83%). The pure product was characterized as its DCHA salt which was prepared in diethyl ether, m.p. 153°–155° C.

EXAMPLE 58

N-(3-Acetylthio-2-methylpropanoyl)-N-phenylglycine

Crude N-(3-acetylthio-2-methylpropanoyl)-N-phenylglycine tert-butyl ester (25 g, 0.0712 mol) was dissolved in a mixture of anisole (40 ml) and trifluoroacetic acid (125 ml). The resulting red solution was stirred overnight at room temperature. The solvent was evaporated and the residue was distributed between ethyl acetate and saturated aqueous sodium bicarbonate. The aqueous sodium bicarbonate layer was acidified cautiously with concentrated hydrochloric acid to pH 4–5. The product was extracted several times into chloroform, washed twice with water, and dried over magnesium sulfate. Filtration and evaporation of the extract afforded the crude product as an orange oil which was further purified by HPLC, eluting with ethyl acetate/n-hexane/acetic acid (40:60:1), to afford pure product (7.5 g., 36%) as a pale yellow oil. The product was crystallized from diethyl ether to afford colorless prisms, m.p. 94°–94.5° C.

EXAMPLE 59

N-(3-Mercapto-2-methylpropanoyl)-N-phenylglycine

Anhydrous ammonia was bubbled for fifteen minutes through methanol (500 ml) and the resulting saturated solution was added to N-(3-acetylthio-2-methylpropanoyl)-N-phenylglycine (13.5 g., 0.0458 mol). The reaction mixture was stirred for an hour and a half at room temperature. Methanol was evaporated on a rotary evaporator and the residue was applied to a column of AG-50W-X2 (Bio-Rad Laboratories) cation exchange resin and eluted with methanol. Methanol was evaporated and the residue was dissolved in chloroform. The chloroform was washed once with water and dried over magnesium sulfate. Filtration and evaporation of the extract afforded a colorless solid (10 g, 90%) which was filtered and washed with a small amount of cold diethyl ether, m.p. 168°–170° C.

EXAMPLE 60

N-(3-Acetylthio-2-methylpropanoyl)-N-(endo-norbornyl)glycine

Crude N-(3-acetylthio-2-methylpropanoyl)-N-(endo-norbornyl)glycine tert-butyl ester (70 g, 0.190 mol) was dissolved in a mixture of anisole (100 ml) and trifluoroacetic acid (200 ml). The resulting solution was stirred at room temperature for two hours. Trifluoroacetic acid was removed in vacuo and the residue was distributed between ethyl acetate and saturated sodium bicarbonate. The aqueous bicarbonate phase was separated and washed twice with ethyl acetate and then acidified cautiously to pH 4–5 with concentrated hydrochloric acid. The product was extracted into chloroform and washed twice with water. The organic phase was dried over magnesium sulfate, filtered and evaporated to give crude product as an orange oil (20 g). The crude product was further purified by HPLC, eluting with ethyl acetate/n-hexane/acetic acid (40:60:1), to give pure product as a pale yellow oil (12 g, 20.2%). The product was characterized as its DCHA salt which was prepared in ether to give colorless crystals, m.p. 116° C.

EXAMPLE 61

N-(3-Acetylthio-2-methylpropanoyl)-N-(3'-pyridylmethyleneglycine ethyl ester To a solution of N-(3-pyridylmethylene)glycine ethyl ester (6.2 g, 0.032 mol) and 3-acetylthio-2-methylpropionic acid (5.2 g, 0.032 mol) in methylene chloride (100 ml) was added dicyclohexylcarbodiimide (6.8 g, 0.0330 mol). Stirring was continued at room temperature overnight. Precipated dicyclohexyurea was filtered and washed with a small amount of cold diethyl ether. Evaporation of the filtrate afforded the crude product as an orange oil (12.5 g). The produce was purified by HPLC using a step gradient procedure. Nonpolar material was eluted using ethyl acetate/ammonium hydroxide (98:2) as eluent. The polar product was eluted using the solvent system of acetonitrile/methanol/ammonium hydroxide (90:8:2) to give pure product as a pale yellow oil (8.4 g, 80%).

EXAMPLE 62

N-(3-Acetylthio-2-methylpropanoyl)-N-(2'-methylene-1'-ethylpyrrolidine)glycine tert-butyl ester To a solution of N-(2'-methylene-1'-ethylpyrrolidine)glycine tert-butyl ester (10.2 g., 0.042 mol) and 3-acetylthio-3-methylpropionic acid (6.8 g, 0.042 mol) in dry methylene chloride (200 ml) chilled in an ice bath was added dicyclohexylcarbodiimide (8.7 g, 0.042 mol). The resulting mixture was stirred overnight at room temperature. Precipitated dicyclohexyurea was filtered and washed with a small amount of methylene chloride. Concentration of the filtrate afforded crude product as a dark auburn oil (18.1 g) which was used without further purification.

EXAMPLE 63

N-(3-Mercapto-2-methylpropanoyl)-N-(2'-methylene-1'-ethylpyrrolidine)glycine Crude N-(3-acetylthio-2-methylpropanoyl)-N-(2'-methylene-1'-ethylpyrrolidine)glycine tert-butyl ester (10.0 g, 0.026 mol) was dissolved in a mixture of anisole (20 ml) and trifluoroacetic acid 60 ml). The resulting solution was stirred at room temperature for two hours. Trifluoroacetic acid was evaporated in vacuo and the residue was distributed between ethyl acetate and saturated aqueous sodium bicarbonate. The aqueous bicarbonate phase was separated and washed twice with ethyl acetate. The aqueous bicarbonate phase was then saturated with ammonium chloride and placed in a heavier than water continuous liquid extractor. The product was continuously extracted into chloroform over 16 hours. The chloroform was dried over magnesium sulfate, filtered and evaporated to give the mercaptan as an oil (4.3 g, 57%). The product was characterized as its DCHA salt which was prepared in ether to give colorless crystals, m.p. 120°–122° C.

By following the procedures described in the above examples, the following additional compounds were prepared:

N-(3-Mercapto-2-methylpropanoyl)-N-(4-hydroxycyclohexyl)glycine
N-(3-Mercapto-2-methylpropanoyl)-N-(4-methoxycyclohexyl)glycine
N-(3-Mercapto-2-methylpropanoyl)-N-(2-hydroxynorbornyl)glycine
N-(3-Mercapto-2-methylpropanoyl)-N-(2-methoxynorbornyl)glycine
N-(3-Mercapto-2-methylpropanoyl)-N-(1-adamantyl)glycine
N-(3-Mercapto-2-methylpropanoyl)-N-(furyl)glycine
N-(3-Mercapto-2-methylpropanoyl)-N-(5-benzofuryl)glycine
N-(3-Mercapto-2-methylpropanoyl)-N-(cyclopropyl)glycine
N-(3-Mercapto-2-methylpropanoyl)-N-(p-trifluorophenyl)glycine
N-(3-Mercapto-2-methylpropanoyl)-N-(phenyl)glycine
N-(3-Mercapto-2-methylpropanoyl)-N-(furfuryl)glycine
N-(3-Mercapto-2-methylpropanoyl)-N-(3-methylmercaptophenyl)glycine
N-(3-Mercapto-2-methylpropanoyl)-N-(cyclobutyl)glycine
N-(3-Mercapto-2,2-dimethylpropanoyl)-N-(3-thienyl)glycine
N-(3-Acetylthio-2-methylpropanoyl)-N-(1-methylcyclohexyl)glycine
N-(3-Benzoylthio-2-methylpropanoyl)-N-(3-thiazolyl)glycine
N-(3-Mercapto-3-methylbutanoyl)-N-(2-benzothiolyl)glycine
N-(2-Mercapto-2-methylpropanoyl)-N-(4-tetrahydrothiopyranyl)glycine
N-(4-Mercapto-2-methylbutanoyl)-N-(1-methylcycloheptyl)glycine
N-(3-Mercapto-2-methylpropanoyl)-N-(9-fluorenyl)glycine
N-(3-Mercapto-2-methylpropanoyl)-N-1-(2-thienyl)ethylglycine
N-(3-Mercapto-2-methylpropanoyl)-N-(3-tetrahydrothienyl)glycine
N-(3-Mercapto-2-methylpropanoyl)-N-(N-ethylpiperdine-3-yl)glycine
N-(3-Mercapto-2,3-dimethylbutanoyl)-N-(2-chlorocyclopentyl)glycine
N-(3-Mercapto-2,2-dimethylbutanoyl)-N-(2-hydroxycyclopentyl)glycine
N-(2-Mercaptomethylbutanoyl)-N-2-(1-indol-3-yl-propyl)glycine
N-(3-Mercapto-2-methylpropanoyl)-N-2-methylenethienylglycine
N-(3-Mercapto-2-methylpropanoyl)-β-(2-thienyl)alanine
N-(3-Mercapto-2-methylpropanoyl)-β-(2-pyridyl)alanine
N-(3-Mercapto-2-methylpropanoyl)-methylalanine
N-(3-acetylthio-2-methylpropanoyl)-N-(cyclopropyl)glycine
N-(Acetylthio-2-methylpropanoyl)-N-(cyclobutyl)glycine
N-(3-Acetylthio-2-methylpropanoyl)-N-(cyclopentyl)glycine
N-(3-Acetylthio-2-methylpropanoyl)-N-(exo-norbornyl)glycine
N-(3-Acethylthio-2-methylpropanoyl)-N-(3,4-methylenedioxyphenyl)glycine
N-(3-Acetylthio-2-methylpropanyl)-N-(endo-norbornyl)glycine
N-(3-Mercapto-2-methylpropanoyl)-N-(m-fluorophenyl)glycine
N-(3-Mercapto-2-methylpropanoyl)-N-(1-methyl exo-norbornyl)glycine
N-(3-Mercapto-2-methylpropanoyl)-N-(2-mercaptocyclopentyl)glycine
N-(3-Mercapto-2-methylpropanoyl)-N-(2-mercaptocyclohexyl)glycine
N-(3-Mercapto-2-methylpropanoyl)-N-(1,4-ethylendioxyphenyl)glycine
N-(3-Mercapto-2-methylpropanoyl)-N-(cycloheptyl)glycine
N-(3-Mercapto-2-methylpropanoyl)-N-(2-ethylthio)glycine
N-(3-Mercapto-2-methylpropanoyl)-N-(4-aminopyridyl)glycine
N-(3-Acetylthio-2-methylpropanoyl)-N-(1-isoquinolyl)glycine
N-(3-Acetylthio-2-methylpropanoyl)-N-(3-benzonitrile)glycine
N-(3-Acetylthio-2-methylpropanoyl)-N-(2-pyrimidyl)glycine
N-(3-Acetylthio-2-methylpropanoyl)-N-(2-benzimidazoyl)glycine
N-(3-Mercapto-2-methylpropanoyl)-N-(1-methylcyclopropyl)glycine
N-(3-Mercapto-2-methylpropanoyl)-N-(indan-2-yl)glycine
N-(3-Mercapto-2-methylpropanoyl)-N-(1-methylcyclobutyl)glycine
N-(3-Mercapto-2-methylpropanoyl)-N-(1,2,3,4-tetrahydronaphth-1-yl)glycine
N-(3-Mercapto-2-methylpropanoyl)-N-(1,methylcyclopentyl)glycine
N-(3-Mercapto-2-methylpropanoyl)-N-(tetrahydrothiophene-1,1-dioxide3-yl)glycine The compounds of the present invention have demonstrated potent activity (of the order $I_{50}$ of 0.017 to 0.030 micromols) in inhibiting the angiotensin converting enzyme (ACEI activity) when tested by the method described in Science 196, 441–4 (1977). As such, these compounds would be very useful in the treatment of hypertension.

The compounds of the present invention are somewhat structurally related to the compounds disclosed in German Offenlengunsschriften Nos. 2,717,548 and 2,753,824. However, the compounds disclosed in these publications posses an ACEI activity of about one three hundredth shown by the compounds of the present invention.

Table I below lists the ACEI activity of representative compounds of the present invention. The $I_{50}$ value represents the amount in micromols required to give an inhibitive effect of 50% in the tests using the procedure described in the Science article.

TABLE 1

$$R_7-S-CH_2-CH(CH_3)-\underset{\underset{O}{\|}}{C}-\underset{\underset{M}{|}}{N}-CH_2-CO_2H$$

| M | $R_7$ | $I_{50}$ |
|---|---|---|
| Cyclopropyl | H | 0.027 |
| Cyclopentyl | H | 0.017 |
| Cyclopentyl | $CH_3CO$ | 0.044 |
| Cyclohexyl | H | 0.029 |
| Cycloheptyl | H | 0.031 |
| Cycloheptyl | $CH_3CO$ | 0.088 |
| exo-Norbornyl | H | 0.025 |
| exo-Norbornyl | $CH_3CO$ | 0.022 |
| $H_3CS(CH_2)_3$ | H | 0.055 |
| $H_3CO(CH_2)_2$ | H | 0.095 |

The compounds of the present invention also demonstrated potent antihypertensive activity when administered orally to angiotensin I-induced hypertensive rats.

Table II, below, lists the antihypertensive activity of some representative compounds of the present invention. The $ID_{50}$ is the dose in mg. compound/kg; given orally, required to effect a 50% reduction in the angiotension I-induced hypertension.

TABLE II $$R_7-S-CH_2-CH(CH_3)-\underset{\underset{O}{\|}}{C}-\underset{\underset{M}{|}}{N}-CH_2-CO_2H$$

| M | $R_7$ | $I_{50}$ |
|---|---|---|
| exo-Norbornyl | $CH_3CO$ | 0.06 |
| Cyclopentyl | $CH_3CO$ | 0.16 |
| exo-Norbronyl | H | 0.11 |
| Cyclopentyl | H | 0.15 |
| Phenyl | $CH_3CO$ | 0.23 |
| Cyclopropyl | $CH_3CO$ | 0.13 |
| Cylcobutyl | H | 0.21 |
| Cyclopropyl | H | 0.14 |
| 2-Indanyl | H | 0.16 |
| Cycloheptyl | H | 0.021 |

The compounds of the present invention may be administered orally or parenterally in the treatment of hypertension, and it will be within the professional judgment and skill of the practitioner to determine the exact amount to be administered.

We claim:

1. Compounds of the structure

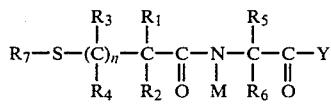

wherein
  $R_1$, $R_2$, $R_3$, $R_4$, $R_5$ and $R_6$ are independently hydrogen, lower alkyl, lower alkenyl, lower alkenyl, or phenyl-lower alkyl, wherein the lower alkyl, lower alkenyl and lower alkynyl groups have up to 6 carbon atoms,
  n is an integer from 0 to 4,
  M is lower alkenyl, lower alkynyl, cycloalkyl, cycloalkyl-lower alkyl, bicycloalkyl, fused arylcycloalkyl, phenyl, lower alkylphenyl, phenyl-lower alkyl, hydroxyphenyl, methylenedioxyphenyl, bicycloalkyl-lower alkyl, lower alkylthio-lower alkyl, lower alkoxy-lower alkyl, halophenyl or, lower alkylthiophenyl, wherein the lower alkyl, lower alkenyl and lower alkynyl groups contain up to 6 carbon atoms and the cycloalkyl, cycloalkyl lower alkyl, bicycloalkyl, and fused aryl-cycloalkylkyl groups contain from 3 to 16 carbon atoms,
  Y is hydroxy, lower alkoxy having 1 to 6 carbon atoms or amino,
  $R_7$ is hydrogen, lower alkanoyl, benzoyl, ZS or

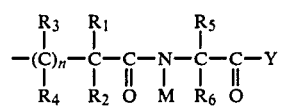

wherein the lower alkanoyl contains up to 6 carbon atoms Z is hydrogen, lower alkyl, hydroxy-lower alkyl, amino-lower alkyl, or a radical of the formula $$-(C)_n-\underset{\underset{R_4}{|}}{\overset{\overset{R_3}{|}}{C}}-\underset{\underset{R_2}{|}}{\overset{\overset{R_1}{|}}{C}}-\underset{\underset{M}{|}}{N}-\underset{\underset{R_6}{|}}{\overset{\overset{R_5}{|}}{C}}-\overset{\overset{}{\|}}{C}-Y$$

wherein $R_1$, $R_2$, $R_3$, $R_4$, $R_6$, n, M and Y are as defined above, and where Y is hydroxy, their non-toxic, pharmaceutically acceptable alkali metal, alkaline earth metal, and amine salts.

2. A compound according to claim 1 where $R_1$, $R_2$, $R_3$, $R_4$, $R_5$ and $R_6$ are hydrogen or lower alkyl.

3. A compound according to claim 2 wherein n is 1.

4. A compound according to claim 3 wherein Y is hydroxy.

5. A compound according to claim 4 wherein $R_1$, $R_3$, $R_4$, $R_5$ and $R_6$ are hydrogen and $R_2$ is lower alkyl.

6. A compound according to claim 5 wherein $R_2$ is methyl.

7. A compound according to claim 6 wherein $R_7$ is hydrogen.

8. A compound according to claim 6 wherein $R_7$ is lower alkanoyl.

9. A compound according to claim 8 wherein $R_7$ is acetyl.

10. A compound according to claim 7 wherein M is cyclopropyl.

11. A compound according to claim 7 wherein M is cyclopentyl.

12. A compound according to claim 9 wherein M is cyclopentyl.

13. A compound according to claim 7 wherein M is exo-norbornyl.

14. A compound according to claim 9 wherein M is exo-norbornyl.

15. A compound according to claim 7 wherein M is cyclobutyl.

16. A compound according to claim 7 wherein M is cycloheptyl.

17. A method of reducing the blood pressure in mammals having hypertension which comprises administering an effective amount of a compound of claim 1.

18. A compound according to claim 7 wherein M is 2-indanyl.

* * * * *

REEXAMINATION CERTIFICATE (262nd)

United States Patent [19]
Suh et al.

[11] B1 4,256,761
[45] Certificate Issued Oct. 9, 1984

[54] ANTIHYPERTENSIVE AMIDES

[75] Inventors: John T. Suh, Greenwich, Conn.; Jerry W. Skiles, Tuckahoe, N.Y.; Bruce E. Williams, Yorktown Heights, N.Y.; Alfred Schwab, Williston Park, N.Y.

[73] Assignee: USV Pharmaceutical Corporation, Tuckahoe, N.Y.

Reexamination Request:
No. 90/000,359, Apr. 14, 1983

Reexamination Certificate for:
Patent No.: 4,256,761
Issued: Mar. 17, 1981
Appl. No.: 57,175
Filed: Jul. 13, 1979

[51] Int. Cl.³ .................. A61K 31/36; A61K 31/265; C07C 149/43; C07C 149/40
[52] U.S. Cl. .................. 424/282; 424/301; 424/319; 424/320; 424/311; 560/9; 560/16; 560/17; 560/125; 560/153; 560/155; 562/426; 562/507; 562/556; 564/154; 260/455 R; 260/455 B; 260/340.5 R
[58] Field of Search .................. 260/455 R, 455 B; 424/282, 309, 319, 320, ; 560/9, 16, 17, 125, 153, 155; 562/426, 507, 556; 549/444; 564/162, 192

[56] References Cited

U.S. PATENT DOCUMENTS

| | | | |
|---|---|---|---|
| 3,869,492 | 3/1975 | Biel et al. | 260/463 |
| 4,053,651 | 10/1977 | Ondetti et al. | 424/319 |
| 4,091,024 | 5/1978 | Ondetti | 546/189 |
| 4,116,962 | 9/1978 | Ondetti et al. | 546/206 |

FOREIGN PATENT DOCUMENTS

| | | | |
|---|---|---|---|
| 2717548 | 5/1977 | Fed. Rep. of Germany | 424/319 |
| 2753824 | 6/1978 | Fed. Rep. of Germany | 548/551 |
| 1500576 | 2/1978 | United Kingdom | 424/319 |
| 1577415 | 10/1980 | United Kingdom | 424/319 |

*Primary Examiner*—Alan L. Rotman

[57] ABSTRACT

Compounds of the structure:

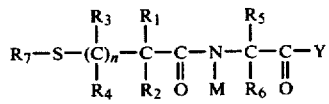

wherein
$R_1$, $R_2$, $R_3$, $R_4$, $R_5$, and $R_6$ are hydrogen, alkyl, alkenyl, alkynyl, phenyl-alkyl, or cycloalkyl,
n is an integer from 0 to 4 inclusive,
M is alkenyl, alkynyl, cycloalkyl, cycloalkyl-alkyl, polycycloalkyl, polycyclo-alkyl-alkyl, aryl, aralkyl, heteroaryl, heteroaryl-alkyl, hetero-cycloalkyl, hetero-cycloalkyl-alkyl, alkoxyalkyl, alkylthioalkyl, alkylamino-alkyl, dialkylamino-alkyl, fused aryl-cycloalkyl, fused aryl-cycloalkyl-alkyl, fused heteroaryl-cycloalkyl, or fused heteroaryl-cycloalkyl-alkyl,
Y is hydroxy, alkoxy, amino, or substituted amino, aminoalkanoyl, aryloxy, aminoalkoxy, or hydroxyalkoxy, and
$R_7$ is hydrogen, alkanoyl, carboxylalkanoyl, hydroxyalkanoyl, amino-alkanoyl, cyano, amidino, carbalkoxy, ZS, or $$\begin{matrix} ZSC \\ \parallel \\ O \end{matrix}$$

wherein Z is hydrogen, alkyl, hydroxyalkyl, aminoalkyl or the radical

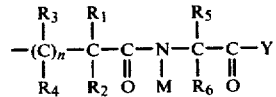

wherein $R_1$, $R_2$, $R_3$, $R_4$, $R_5$, $R_6$, n, M and Y are as described above; and where Y is hydroxy their non-toxic, pharmaceutically acceptable alkali metal, alkaline earth metal, and amine salts.

REEXAMINATION CERTIFICATE ISSUED UNDER 35 U.S.C. 307.

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 22, lines 56-62:

The compounds of the present invention are somewhat structurally related to the compounds disclosed in German Offenlengunsschriften Nos. 2,717,548 and 2,753,824. [However, the compounds disclosed in these publications posses an ACEI activity of about one three hundredth shown by the compounds of the present invention.]

AS A RESULT OF REEXAMINATION, IT HAS BEEN DETERMINED THAT:

Claims 1-18 are cancelled.

New claims 19-37 are added and determined to be patentable.

19. *Compounds of the structure*

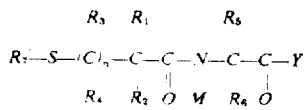

*wherein*
*$R_1$, $R_2$, $R_3$, $R_4$, $R_5$ and $R_6$ are independently hydrogen, lower alkyl, lower alkenyl, or phenyl-lower alkyl, wherein the lower alkyl, lower alkenyl and lower alkynyl groups have up to 6 carbon atoms,*
*n is an integer from 0 to 4,*
*M is cycloalkyl, cycloalkyl-lower alkyl, bicycloalkyl, fused arylcycloalkyl, lower alkylphenyl, hydroxyphenyl, methylenedioxyphenyl, bicycloalkyl-lower alkyl, halophenyl or alkylthiophenyl, and contains from 3 to 16 carbon atoms,*
*Y is hydroxy, lower alkoxy having 1 to 6 carbon atoms or amino,*
*$R_7$ is hydrogen, lower alkanoyl, benzoyl, ZS or*

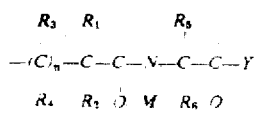

*wherein the lower alkanoyl contains up to 6 carbon atoms Z is hydrogen, lower alkyl, hydroxy-lower alkyl, amino-lower alkyl, or a radical of the formula*

*wherein $R_1$, $R_2$, $R_3$, $R_4$, $R_6$, n, M and Y are as defined above, and where Y is hydroxy, their non-toxic, pharmaceutically acceptable alkali metal, alkaline earth metal, and amine salts.*

20. *A compound according to claim 19 wherein n is 1.*

21. *A compound according to claim 19 where $R_1$, $R_2$, $R_3$, $R_4$, $R_5$ and $R_6$ are hydrogen or lower alkyl.*

22. *A compound according to claim 21 wherein n is 1.*

23. *A compound according to claim 22 wherein Y is hydroxy.*

24. *A compound according to claim 23 wherein $R_1$, $R_3$, $R_4$, $R_5$ and $R_6$ are hydrogen and $R_2$ is lower alkyl.*

25. *A compound according to claim 24 wherein $R_2$ is methyl.*

26. *A compound according to claim 25 wherein $R_7$ is hydrogen.*

27. *A compound according to claim 25 wherein $R_7$ is lower alkanoyl.*

28. *A compound according to claim 27 wherein $R_7$ is acetyl.*

29. *A compound according to claim 26 wherein M is cyclopropyl.*

30. *A compound according to claim 26 wherein M is cyclopentyl.*

31. *A compound according to claim 27 wherein M is cyclopentyl.*

32. *A compound according to claim 26 wherein M is exo-norbornyl.*

33. *A compound according to claim 27 wherein M is exo-norbornyl.*

34. *A compound according to claim 26 wherein M is cyclobutyl.*

35. *A compound according to claim 26 wherein M is cycloheptyl.*

36. *A method of reducing the blood pressure in mammals having hypertension which comprises administering an effective amount of a compound of claim 19.*

37. *A compound according to claim 26 wherein M is 2-indanyl.*

* * * * *